(12) United States Patent
Spaeder

(10) Patent No.: US 7,504,954 B2
(45) Date of Patent: Mar. 17, 2009

(54) RADIO FREQUENCY IDENTIFICATION PHARMACEUTICAL TRACKING SYSTEM AND METHOD

(76) Inventor: Jeffrey A. Spaeder, 301 Warren Ave., Apartment 420, Baltimore, MD (US) 21230

( * ) Notice: Subject to any disclaimer, the term of this patent is extended or adjusted under 35 U.S.C. 154(b) by 365 days.

(21) Appl. No.: 11/082,257

(22) Filed: Mar. 17, 2005

(65) Prior Publication Data

US 2006/0210626 A1 Sep. 21, 2006

(51) Int. Cl.
G08B 23/00 (2006.01)

(52) U.S. Cl. .............. 340/573.1; 340/691.6; 340/572.1; 128/204.18

(58) Field of Classification Search .............. 340/573.1, 340/568.1, 572.1–572.9, 691.1, 691.6; 206/528, 206/534, 828, 538; 128/200.14, 200.24, 128/204.18
See application file for complete search history.

(56) References Cited

U.S. PATENT DOCUMENTS

| | | | |
|---|---|---|---|
| 4,844,076 A | | 7/1989 | Lesho et al. |
| 5,016,172 A | | 5/1991 | Dessertine |
| 5,200,891 A | * | 4/1993 | Kehr et al. ..................... 221/2 |
| 5,710,551 A | | 1/1998 | Ridgeway |
| 5,950,632 A | * | 9/1999 | Reber et al. ................. 128/898 |
| 6,294,999 B1 | * | 9/2001 | Yarin et al. .............. 340/573.1 |
| 6,335,907 B1 | * | 1/2002 | Momich et al. .............. 368/10 |
| 6,366,206 B1 | * | 4/2002 | Ishikawa et al. ......... 340/573.1 |
| 6,380,858 B1 | * | 4/2002 | Yarin et al. .............. 340/573.1 |
| 6,440,069 B1 | * | 8/2002 | Raymond et al. ........... 600/300 |
| 6,634,560 B1 | * | 10/2003 | Grabau ....................... 235/492 |
| 6,800,060 B2 | | 10/2004 | Marshall |
| 7,178,729 B2 | * | 2/2007 | Shaffer et al. ............... 235/385 |
| 7,223,247 B2 | * | 5/2007 | Madsen ...................... 600/561 |
| 7,253,716 B2 | * | 8/2007 | Lovoi et al. ................ 340/10.1 |
| 2002/0145526 A1 | | 10/2002 | Friedman et al. |
| 2003/0009088 A1 | | 1/2003 | Korth et al. |
| 2003/0144926 A1 | | 7/2003 | Bodin et al. |
| 2003/0164401 A1 | | 9/2003 | Andreasson et al. |
| 2004/0008123 A1 | | 1/2004 | Carrender et al. |
| 2004/0046020 A1 | | 3/2004 | Andreasson et al. |

OTHER PUBLICATIONS

Kevin Bonsor; "How Smart Labels Will Work"; http://electronics.howstuffworks.com/smart-label1.htm (pp. 1-3); (Jan. 19, 2005).
"The IT Revolution: The Best Thing Since The Bar-Code"; The Economist; (pp. 1-2); (Feb. 8, 2003).

* cited by examiner

*Primary Examiner*—Daniel Previl
(74) *Attorney, Agent, or Firm*—The Webb Law Firm

(57) ABSTRACT

An ingestible dosage form includes a pill containing a pharmaceutical content and an RF tag associated with the pill. The RF tag is configured to output a wireless response signal in response to a wireless excitation signal received by the RF tag from an RF reader. The ingestible dosage form includes memory for storing pill identifying information. The wireless response signal includes the pill identifying information which may be received and processed by the RF reader. A system for monitoring patient medicine intake compliance includes a monitoring device placed within communicative proximity of ingestible dosage forms to transmit the wireless excitation signal and receive the wireless response signal including pill identifying information from the ingestible dosage forms. A device for determining an identity of a pill and quantity thereof ingested by an individual includes a nasogastric/orogastric tube having an RF tag reader attached thereto for detecting RF tagged pills.

4 Claims, 3 Drawing Sheets

RADIO FREQUENCY IDENTIFICATION PHARMACEUTICAL TRACKING SYSTEM AND METHOD

BACKGROUND OF THE INVENTION

1. Field of the Invention

The present invention relates generally to a pill having a radio frequency tag associated therewith that allows for monitoring patient medicine intake compliance and determining an identity of the pill and quantity thereof ingested by an individual.

2. Description of the Related Art

Despite the life-saving benefits of many prescription medications, only 30%-70% of patients adhere to the prescribed intake of their medications, and less than 50% reliably adhere to long-term prescriptions. Medication non-adherence affects the healthcare industry at both a patient level and at a pharmaceutical corporate level. Patients are deprived of the benefits of the medications, which can result in increased hospitalizations and mortality. It has been estimated that medication non-adherence accounts for 11% of all hospitalizations for the elderly, with more significant consequences in sub-groups of patients with severe illnesses such as heart failure where 24%-43% of all hospital admissions have been attributed to medication non-adherence. Non-adherence also has financial consequences to pharmaceutical companies due to lost revenue. It has been estimated that the yearly loss of revenue for cholesterol lowering medications due to non-adherence is $3.9 billion with close to $70 billion lost for all drug classes.

Identification of patients who do not adhere to medical therapy is challenging because patients underestimate the frequency with which they fail to take medications. Although some drugs can be detected by diagnostic serum or urine assays, such tests are not a feasible way of monitoring long-term adherence because few medications can be detected with existing tests and the cost and logistics of routinely performing such tests would be prohibitive. Specifically, although a chemical agent may be added to pills which could be detected for adherence, there are several significant problems with this approach. First, a large number of additives would need to be identified given the thousands of prescription medications currently available. Second, these agents would need to be absorbed and detected in blood or urine analysis, or if not absorbed, then be detected in feces. Absorbed chemicals would have to undergo extensive regulatory review to be deemed safe, and then the levels of the chemicals would need to be correlated with liver and kidney dysfunction, which are common in people taking medications. Collection of non-absorbed chemicals or markers would also be challenging. Even if a suitable number of unique, well-absorbed, biologically inert chemicals were identified, in-vivo detection would be logistically difficult and expensive. It is unlikely that a patient who proves to be non-adherent with taking pills would be more compliant with regularly scheduled blood or urine analysis.

Because most medications are in the form of a pill, monitoring of medication decanting may be used to monitor compliance. Specifically, electronic Medication Event Monitoring Systems (MEMS) have been used in studies to assess medication compliance, and in several instances have been used as an adjunct to outpatient monitoring in an effort to improve medication compliance. For example, U.S Pat. Publication No. US 2004/0008123 to Carrender et al. discloses a sensing device integrated into a pill container to sense the opening thereof. Similarly, U.S. Pat. No. 5,016,172 to Dessertine discloses a patient compliance and status monitoring system that utilizes a cap-opening counting device to record the number of cap openings. A further example is disclosed in U.S Pat. Publication No. 2003/0009088 to Korth et. al wherein a pill dispenser is equipped with a transmitter configured to transmit a message that a drug has been removed from the dispenser. However, as is evident in the prior art, MEMS devices only record the number of times a bottle was opened, and not how many, if any, pills were removed or what pharmaceutical content was contained in those pills. Additionally, MEMS devices have been found to be. incompatible with complex medical regimens and frequently interfere with personal adherence strategies. Finally, widespread implementation of MEMS devices would require significant logistical support at a pharmacy/pharmacist level.

Due to patients not accurately reporting medication adherence and the fact that monitoring of adherence at the level of the medication dispensing container is unlikely to be feasible, it is increasingly clear that other forms of medication adherence may be appropriate. It is, therefore, desirable to overcome the above problems and others by providing a system and method for quickly, efficiently and accurately qualifying and quantifying patient medication to not only monitor patient medicine intake compliance, but also to determine an identity of any pills and quantity thereof ingested by an individual.

SUMMARY OF THE INVENTION

Accordingly, I have invented an ingestible dosage form including a pill containing a pharmaceutical content and an RF tag attached to the pill, at least partially received in the pill, or fully embedded in the pill. The RF tag is configured to output a wireless response signal in response to a wireless excitation signal received by the RF tag from an RF reader. The ingestible dosage form includes memory for storing pill identifying information in the form of data representative of a unique identification code, pharmaceutical content data, manufacturer data, and/or expiration data relating to the ingestible dosage form. The wireless response signal includes the transmission of the data so that the data may be received and processed by the RF reader.

Additionally, I have invented a system for remotely monitoring patient medicine intake compliance including a monitoring device having a unique identifier associated therewith. The monitoring device is designed to be placed within communicative proximity of a plurality of pills each having corresponding RF tags associated therewith. The monitoring device is configured to transmit at least one wireless excitation signal, wherein the at least one wireless excitation signal is configured to cause at least one of the plurality of RF tags to transmit a wireless response signal including pill identifying information. The monitoring device is also configured to receive the wireless response signal from the at least one RF tag and then transmit the unique identifier of the monitoring device and the pill identifying information of the at least one RF tag. The system also includes a computer system configured to receive the unique identifier of the monitoring device and the pill identifying information of the at least one RF tag.

The practical application of utilizing RF tagged pills is that a healthcare provider, or other persons, such as caretakers, may be made aware of the type of pills inside one or more medication dispensing containers and the amount of those pills that were ingested by an individual over a specified time interval. Specifically, the rate at which the RF tagged pills were removed from communicative proximity of the monitoring device would correspond to the rate at which the patient was taking the pills. This approach has significant implications for the delivery of healthcare. Namely, adherence with medical therapy may be monitored in real time and non-adherent patients may quickly and efficiently be identified. Using such information, healthcare providers may institute appropriate interventions or alter prescriptions to improve patient medication adherence. Equally important, RF tagging of pills may permit passive collection of the types of medications a patient was taking, rather than having to query pharmacy databases or rely upon healthcare providers to input such information into a centralized database. Additionally, the health care provider may be immediately notified if incompatible drugs potentially resulting in adverse drug interactions are detected within communicative proximity of the monitoring device.

The use of RF tags to monitor outpatient medication adherence is a novel application of existing technology, which addresses a significant need in the medical community. Prospective advocates of RF tagging of pills may include, but are not limited to:

1. Pharmaceutical Companies—These companies lose billions of dollars in lost sales due to patient non-adherence of approved medications for which prescriptions have already been written. Pharmaceutical companies are actively seeking methods to improve outpatient medication adherence and would be very interested in an approach which would passively identify medication non-adherence;
2. Healthcare Providers—Home monitoring that identifies exactly which medications a patient takes will reduce confusion about the patient's medical regimen and aid in adjusting or adding additional medications;
3. Hospitals—Electronic monitoring of medication dosing of inpatients will improve patient safety and decrease nursing paperwork with associated increases in efficiency;
4. Drug Research Organizations (including Pharmaceutical Companies)—Monitoring of study medication administration during clinical studies will enable correlation with dosing and effect;
5. Families of Patients—With families more geographically isolated, the ability to monitor medication adherence of parents will give peace of mind to many adult children;
6. Patients—Detection of drugs that may have possible interactions and optimization of drug dosing schedule will reduce adverse events and maximize the benefits of the medications. Automatic refill capabilities will reduce the logistics required to keep medications readily available; and
7. Insurance Companies—Although increased adherence to medications may transiently increase pharmacy claims for insurers, long-term medication adherence will improve clinical outcomes. Because commercial health insurance plans have considerable client turnover, the plans may be less interested in increasing patient adherence than long-term insurers such as the Veterans' Administration, Department of Defense, Medicare and state Medicaid agencies.

Due to the initial cost and logistic complexity of such a technology, the widespread use of RF tags to track medication adherence will not occur immediately. It is anticipated that a phased introduction of the technology would occur that will enable the technology to be used in the areas of greatest need followed by a gradual introduction into less acute areas. A proposed phase-in would include high value medications where adherence is important (e.g., narcotics abuse prevention, oral oncology medications, long-term treatment of highly infectious diseases, short-term treatment of potentially fatal infections); medications undergoing Phase II-III outpatient studies; psychiatric medications (especially for schizophrenia and depression); and high value long-term medications (e.g., cholesterol lowering medications, advanced antihypertensive and diabetic medications, anti-retroviral medications for HIV).

Furthermore, I have invented a device for determining an identity of a pill and quantity thereof ingested by an individual in emergency situations. The device includes a nasogastric or orogastric tube having a free end (gastric end) adapted for insertion into a stomach of the individual and an RF tag reader attached to the free end of the tube. The RF tag reader is configured to transmit at least one wireless excitation signal to cause an RF tag associated with the ingested pill to transmit a wireless response signal including data stored on the RF tag. The RF tag reader is further configured to receive the wireless response signal from the at least one RF tag and then transmit the data to a computer system configured to display the data. It is to be understood that the device is ordinarily intended for use in an emergency situation, such as a drug overdose, where the individual is unaware of the types and amounts of pills ingested. Thus, the device may be utilized to not only pump or lavage the stomach of the individual, but to also identify the types and amounts of pills ingested. This would give the healthcare provider more detailed information that would allow the individual to be treated more effectively.

Still other desirable features and applications of the invention will become apparent to those of ordinary skill in the art upon reading and understanding the following detailed description, taken with the accompanying drawings, wherein like reference numerals represent like elements throughout.

DETAILED DESCRIPTION OF THE INVENTION

The present invention will now be described with reference to the accompanying figures. It is to be understood that the specific system illustrated in the attached figures and described in the following specification is simply an exemplary embodiment of the present invention.

Figure 1A:
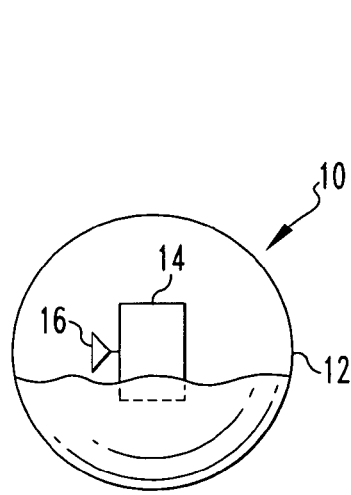
FIG. 1a is a cross-sectional view of an ingestible dosage form according to a first embodiment of the present invention.

With reference to FIG. 1a, a first embodiment ingestible dosage form 10 includes a pill 12 having an RF tag 14 embedded therein. Desirably, the RF tag 14 includes an antenna 16 that is in communicative connection with the RF tag 14. As is known in the art, the antenna 16 may be associated with the RF tag 14 in various configurations including, but not limited to, being integrated within the RF tag 14, extending therefrom, or being affixed thereon. It is to be understood that the RF tag 14 is also commonly referred to as an RFID tag or chip and, therefore, the naming convention of the RF tag 14 as such is not to be construed as limiting the invention. Desirably, the pill 12 contains pharmaceutical content for the treatment of a particular condition. The pharmaceutical content may be similar or identical to the pharmaceutical content present in prior art pills that do not include the RF tag 14. The pill 12 is depicted in round tablet form, however, it is to be understood that pill 12 may be embodied in a number of ingestible dosage forms including, but not limited to capsules, gelatinous capsules, caplets and lozenges. Additionally, it is to be understood that the pill 12 may be of various shapes, dimensions, and dosages. The RF tag 14 is desirably embedded in the ingestible dosage form at the time of manufacture thereof.

As is known in the art, RF tags are presently designed to function as either passive tags, semi-passive tags, or active tags. Briefly, when an RF tag 14 is powered by an interrogation or excitation signal, the RF tag 14 is referred to as a passive tag because it derives the energy necessary for operation from the radio frequency energy transmitted to the RF tag 14. Thus, the passive tag neither includes nor has associated therewith a battery, thereby allowing the passive tag to assume miniaturized dimensions. The RF tag 14 rectifies the resultant energy field and dynamically changes the reflective characteristics of the antenna 16, creating a change in reflectivity that is seen at an RF reader (not shown). In contrast, a battery half empowered semi-passive RF tag operates in a similar fashion by modulating its radio frequency cross-section in order to reflect a delta to the RF reader to develop a communication link. In such instance, the battery is the source of the RF tag's operational power. Finally, in an active RF tag, a transmitter associated with the active RF tag is powered by a battery providing power directly to the RF tag to allow the RF tag to create its own radio frequency energy.

Desirably, the RF tag 14 of the present invention is a passive tag, so that the miniaturized dimensions of the RF tag 14 are conducive to integration of the RF tag 14 with the pill 12. For example, the EM Microelectronics RFID chip model #EM4222 measures 0.5 mm×0.5 mm and the Hitachi RFID Mu-chip measures 0.4 mm×0.4 mm. These exemplary RFID chips when coupled with an antenna may provide data transmissions of up to 5 meters. By comparison, a 40 mg tablet of the drug Simvistatin measures 8 mm×14 mm. Presently, a passive RF tag, such as RF tag 14 may be designed as either an inductively coupled RF tag or a capacitively coupled RF tag. Specifically, the inductively coupled RF tag is considered the traditional type of RF tag as it is generally designed to include a silicon microprocessor, a metal coil, and a coating material. The metal coil may be constructed of copper, aluminum wire, or other ferromagnetic material. Desirably, the metal coil is wound into a circular pattern or other suitable configuration on a transponder, conducive to transmission and reception of an electromagnetic wave, and thereby functioning as the antenna of the RFID tag. The RFID tag transmits signals to the RF reader, with the read distance determined by the size of the coil antenna. A typical and exemplary operating frequency for such a coil antenna is 13.56 MHz. The coating material may be either a glass or polymer material that wraps around the RF tag. Recent advances in RF tag technology have resulted in the design of capacitively coupled RF tags that do away with the metal coil and use a small amount of silicon to perform that same function as an inductively coupled RF tag. Specifically, the capacitively coupled RF tag includes a conductive carbon ink applied to a substrate through printing thereon. However, this is not to be construed as limiting the implementation of RF tags that utilize other printing methods. For example, it may be the case that future RF tags may be ink-jet printed with conductive inks or the like. A silicon chip is attached to printed carbon-ink electrodes on the back of the substrate. This construction allows the capacitively coupled RF tag to be affixed to surfaces. In contrast to the magnetic energy that powers the inductively coupled RF tag, capacitively coupled RF tags are powered by electric fields generated by the reader.

Although the RF tag 14 of the present invention is envisioned to be a passive tag, it is to be understood that with the continual advances of miniaturization in battery technology, it is foreseeable that semi-passive tags and active tags may be substituted for the passive RF tag 14. Additionally, it is envisioned that the RF tag 14 may either be inductively coupled or capacitively coupled. However, this is not to be construed as limiting the design of the RF tag 14 as, understandably, it is anticipated that more advanced designs relating to RFID chips will be developed and implemented in the future.

The RF tag 14 includes memory for storing data containing pill identifying information. Due to the miniaturization of the RF tag, the size of the memory is typically defined in bits of ROM (e.g., 64 bits, 128 bits), however, it is to be understood that with continual improvement in memory technology, the storage capacity of RF tags may increase. The memory may be designed as a single data field or be separated into addressable data fields for storing various portions of the pill identifying information. For example, the pill identifying information data may include, but is not limited to a unique identification code, pharmaceutical content data, manufacturer data, and expiration data. The unique identification code may be an alphanumeric identifier that uniquely identifies the pill 12. The pharmaceutical content data may be an identifier corresponding to the type of pharmaceutical content contained in the pill 12. The manufacturer data may include a code or name of the manufacturer and/or lot number from where the pill 12 derives. The expiration data may be expressed as a month/year combination. It is to be understood that the representations of the aforementioned pill identifying information are for exemplary purposes only. In the instance where a single data field is utilized, the data corresponding to the pill identifying information may be represented as a continuous concatenated data string. Thus, the data string may be decoded into discernable portions of pill identifying information only after receipt of the data string as a whole from the RF tag 14.

The RF tag 14 is configured to output a wireless response signal in response to the wireless excitation signal received by the RF tag 14 from the RF reader. The response signal includes the pill identifying information stored in the memory of the pill 12. Presently, inductively coupled RF tags are configured to operate in either an energy absorption mode or an energy radiation mode. Specifically, the energy absorption mode involves receiving the excitation signal to cause a modulation of the resultant magnetic field during the transmission of the excitation signal. Alternatively, the energy radiation mode involves a continuous oscillation at the resonant frequency for a brief interval even after termination of the excitation signal from the RF reader. During this brief interval, the RF tag has sufficient energy to transmit the response signal to the RF reader. It is to be understood that the transmission of the pill identifying information of the RF tag 14 may be achieved by any of the above-discussed operating modes and any other suitable operating modes that may be developed.

Due to the ingestible nature of the pill 12, it may be desirable to encapsulate the RF tag 14 and antenna 16 with a non-digestible coating (e.g., polymer coating). Thus, after the pharmaceutical portion has been digested, the RF tag 14 would pass through the digestive tract and be expelled with a stool movement of an individual. Alternatively, it is envisioned that the RF tag 14 be constructed of biologically inert components or have minimal concentrations of non-inert compounds so as to make the RF tag 14 non-toxic to the individual.

Figure 1C:
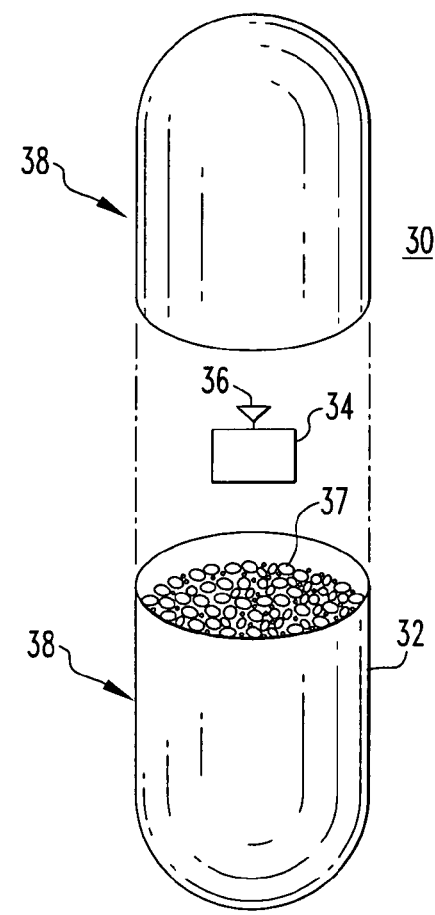
FIG. 1c is an explosive view of the ingestible dosage form according to a third embodiment of the present invention.
Figure 1B:
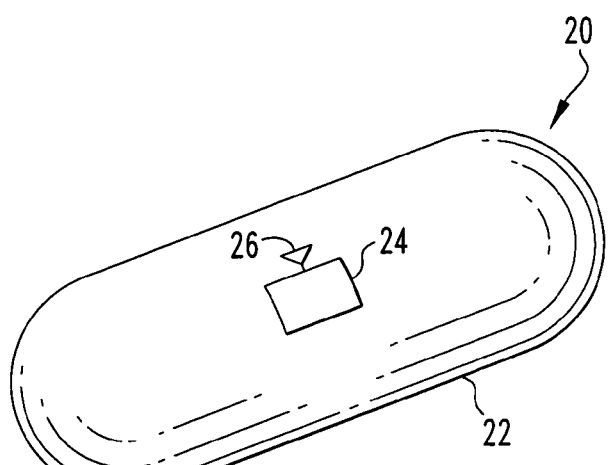
FIG. 1b is a perspective view of the ingestible dosage form according to a second embodiment of the present invention.

With reference to FIGS. 1b and 1c, and with continuing reference to FIG. 1a, a second embodiment ingestible dosage form 20 and a third embodiment ingestible dosage form 30 are shown, respectively. The second embodiment ingestible dosage 20 is a pill 22 in elongated oval tablet form. As is the case with the pill 12, the pill 22 also includes an RF tag 24 with an antenna 26. However, instead of being embedded within the pill 22, the RF tag 24 is affixed to the outside surface of the pill 22. The RF tag 24 may be affixed through a variety of techniques including, but not limited to, adhesion, stamping and printing. The third embodiment ingestible dosage 30 is a pill 32 in elongated capsule form. The pill 32 also includes an RF tag 34 with an antenna 36. Due to the capsule form of the pill 32, pharmaceutical content 37 associated with the pill 32 is contained within a separable shell 38 of the pill 32. The RF tag 34 may be situated among the pharmaceutical content 37 within the shell 38 of the pill 32. It is to be understood that the design characteristics and operation of the RF tag 24 and the RF tag 34 may be similar to that of the RF tag 14. Although not explicitly shown or described herein, an RF tag may also be designed to be partially inserted or embedded into other ingestible dosage forms. With the aforementioned embodiments of pills having RF tags, it is to be understood that a person having ordinary skill in the art is knowledgeable to associate RF tags with other pills having various shapes, dimensions or dosages.

Figure 2:
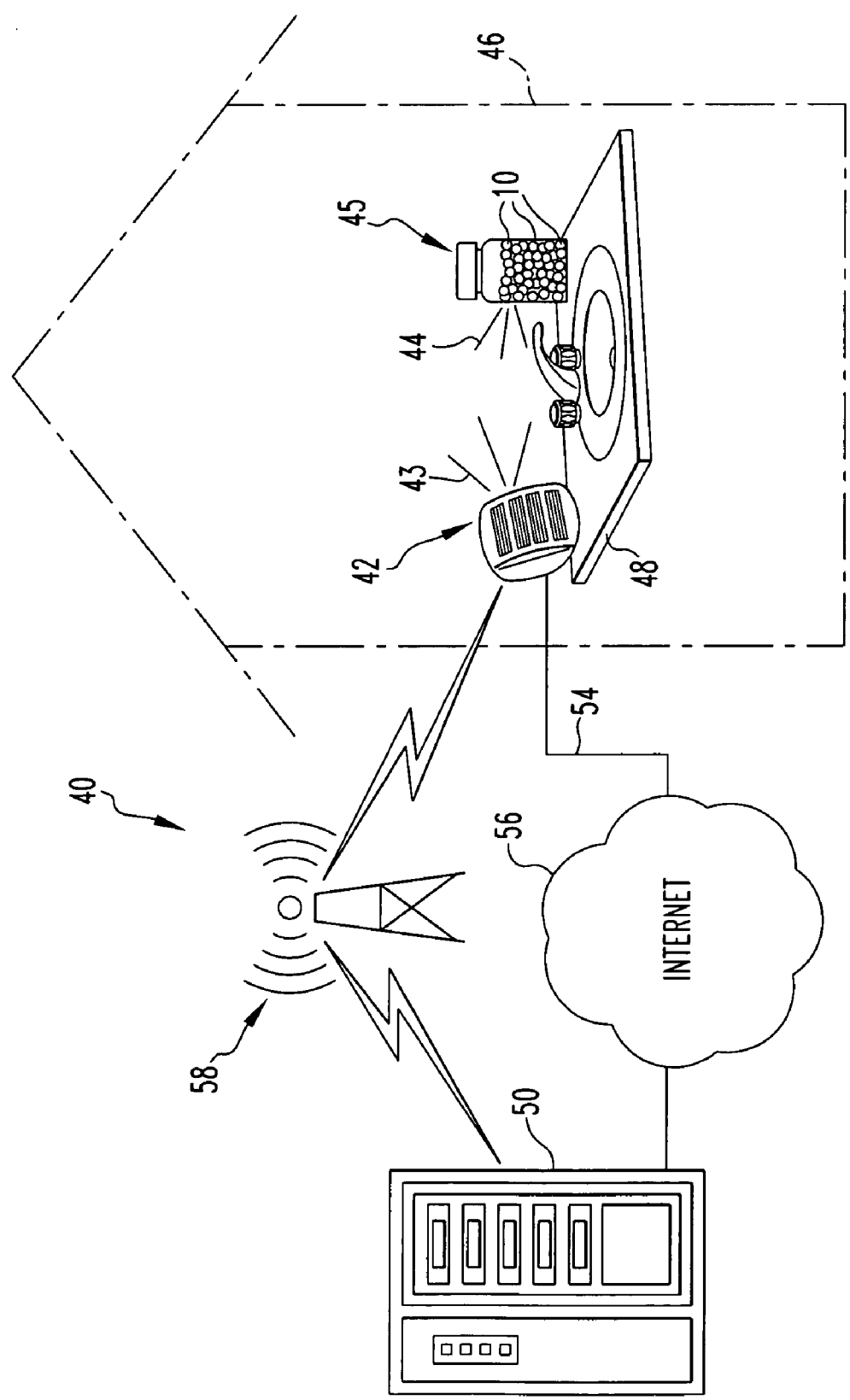
FIG. 2 is a schematic view of a system for monitoring patient medicine intake compliance and status thereof in accordance with the present invention.

With reference to FIG. 2, and with continuing reference to FIGS. 1a-1c, a system 40 for monitoring patient medicine intake compliance and status thereof will now be described. Desirably, a monitoring device 42 is situated within communicative proximity of each of the ingestible dosage forms 10. Essentially, the monitoring device 42 functions as an RFID reader for detecting the presence and identity of the ingestible dosage forms 10. Thus, as is known in the art, an RFID reader, such as the monitoring device 42, is designed with the appropriate hardware and software for performing communicative functions. This includes, but is not limited to a microprocessor, memory and a transmitter/receiver or transceiver antenna. Desirably, the physical appearance, construction material and the dimensions encompassed by the monitoring device 42 may be of any suitable type and are not to be considered as limiting the invention.

The monitoring device 42 is configured to transmit one or more wireless excitation signals 43 to one or more of the ingestible dosage forms 10. It is to be understood that the monitoring device 42 may be configured to transmit various wireless excitation signals of various strengths, frequencies, etc. to selectively target specific ingestible dosage forms. As previously discussed, upon receipt of the wireless excitation signal 43, the ingestible dosage forms 10 transmit the corresponding wireless response signals 44. The monitoring device 42 is configured to receive wireless response signals 44 from corresponding ingestible dosage forms 10 and may utilize anti-collision detection algorithms to simultaneously receive such wireless response signals 44. Desirably, the monitoring device 42 may be configured to transmit the wireless excitation signal 43 at a predetermined time or at predefined intervals. Thus, the patient being monitored need not be pro-active in the medicine intake compliance monitoring. However, alternatively, the monitoring device 42 may be configured to transmit the wireless excitation signal 43 at a manually initiated time.

The monitoring device 42 may be configured to quantify and qualify the resultant pill identifying information data at a local level. For example, after receipt of the wireless response signals 44, the monitoring device 42 may be knowledgeable with respect to the amount and type of ingestible dosage forms 10 that are in communicative proximity with the monitoring device 42. The monitoring system 42 may also be aware of changes in intake and status data relating to the ingestible dosage forms 10 that may or may not be currently within communicative proximity of the monitoring device 42. For example, the monitoring system 42 may determine the identity, manufacturer and expiration date of each ingestible dosage form 10 within an area that is in communicative proximity to the monitoring device. Based upon comparative analysis of quantified and qualified data derived at various intervals, the monitoring system 42 may determine an amount of ingestible dosage forms 10 remaining and the rate of removal thereof within the area that is in communicative proximity to the monitoring device 42.

The monitoring device 42 may be configured to transmit either the quantified and/or qualified data or further derived statistical information to a remote location. Alternatively, the monitoring device 42 may be configured to transmit the wireless response signals 44 or other non-qualified and/or non-quantified variant of data to the remote location for quantification and qualification thereof at the remote location. Furthermore, the monitoring device 42 may include an identifier associated therewith that uniquely identifies the monitoring device 42 from any other monitoring device. Thus, any transmission from the monitoring device 42 to the remote location may be accompanied by the identifier to identify the transmission as originating from the monitoring device 42.

The ingestible dosage forms 10 would be preferably stored within a medication dispensing container 45 or other suitable receptacle that allows the ingestible dosage forms 10 to be stored in a manner conducive to efficient removal thereof. Additionally, such a container would centralize the location of all the ingestible dosage forms 10 and prevent accidental spillage that may inadvertently cause one or more of the ingestible dosage forms 10 to no longer be within communicative proximity of the monitoring device 42. Alternatively to the medication dispensing container 45, the ingestible dosage forms 10 may be contained within pre-packaged dispensing packages or the like.

An exemplary operational environment for the monitoring device 42 and the ingestible dosage forms 10 may be a home 46 of an individual, however, it is to be understood that the present invention may be utilized in other environmental settings (e.g., hospital, nursing home) where ingestible dosage forms are distributed and consumed. An exemplary suitable location within the home 46 may be on a sink 48 in a bathroom, so that the monitoring device 42 may be effectively placed within communicative proximity of the medication dispensing container 45 containing the ingestible dosage forms 10. An assumption is made that the medication dispensing container 45 is not to be removed from the area in communicative proximity with the monitoring device 42. However, it is to be understood that multiple monitoring devices 42 may be placed within the home 46 so as to maintain the area of communicative proximity thereto if the medication dispensing container 45 is removed from communicative proximity of any one of the other monitoring devices 42. In any case, it is to be understood that the environment, the specific location therein, and the positioning of any monitoring device 42 and the ingestible dosage forms 10 are not to be considered as limiting the invention.

An exemplary remote location may be a computer system 50, such as a server and related hardware, that may be hosted and/or managed by a third-party responsible for collecting and processing the un/qualified and un/quantified intake and status data received from the monitoring device 42. The computer system 50 may be communicatively connected to the monitoring device 42 via one or more communication links. Exemplary embodiments of communication links include, but are not limited to wireless communication links 52, such as cellular, paging or other over-the-air networks, or wired communication links 54, such as direct Internet-based links 56 or in-home landline-based phone connections (not shown). Instead of communicating directly with the computer system 50, the monitoring device 42 may transmit the information to a local router (not shown) that may be a part of a local area network, such as a network of computing devices within the home 46. This arrangement may be suitable if more than one monitoring device 42 is utilized by the individual. Based upon the foregoing exemplary communication links, however, it is to be understood that a person having ordinary skill in the art would be sufficiently knowledgeable to implement the necessary hardware and software to route the data from the monitoring device 42 to the computer system 50.

The computer system 50 may also be configured to transmit a signal to the monitoring device 42 to cause the monitoring device 42 to transmit the at least one wireless excitation signal 43. Thus, the monitoring device 42 would not need to be pre-configured to transmit the wireless excitation signal 43 at predetermined times or at predefined intervals. As previously discussed, the monitoring device 42 may be configured to transmit the wireless response signals 44 or other non-qualified and/or non-quantified variation of data to the computer system 50. Therefore, desirably, the computer system 50 may also be configured with the necessary hardware and software to quantify and qualify the received data, as well as enable remote access thereto by authorized personnel. Thus, at some given point, qualified and/or quantified data relating to the individual's medicine intake compliance monitoring is stored on the computer system 50. This data may then be transmitted to other computer systems for viewing by the patient's physician or other healthcare entities involved in the treatment of the patient.

Figure 3:
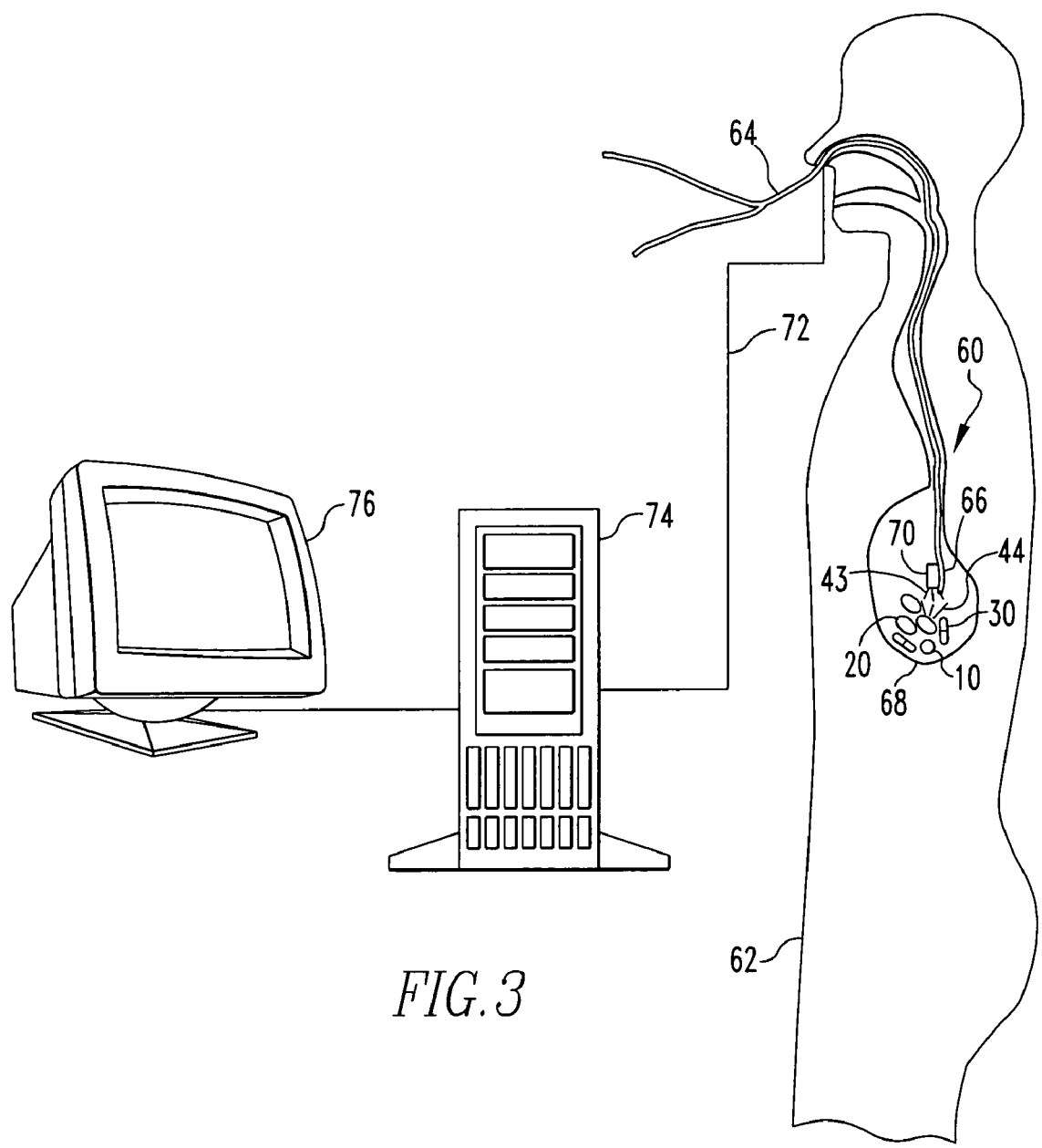
FIG. 3 is a schematic view of a device for determining an identity of the ingestible dosage form and quantity thereof ingested by an individual.

With reference to FIG. 3, and with continuing reference to FIGS. 1a-1c and FIG. 2, a stomach pill detection device 60 is shown. The stomach pill detection device 60 is designed to determine an identity of RF tagged ingestible dosage forms, such as the ingestible dosage forms 10, 20, 30, and quantity thereof ingested by an individual 62. Specifically, the stomach pill detection device includes a nasogastric or orogastric tube 64 having a free end 66, or gastric end, adapted for insertion into a stomach 68 of the individual 62. An RF tag reader 70 is attached to the free end 66 of the tube 64. A communication line 72 may run along the length of the tube 64 to communicatively connect the RF tag reader 70 with a computer 74. The RF tag reader 70 may function similarly to the monitoring device 42 of FIG. 2. Thus, the RF tag reader 70 is configured to transmit at least one wireless excitation signal 43 that causes the RF tag associated with any one of the ingestible dosage forms 10, 20, 30 to transmit a wireless response signal 44 to the RF tag reader 70. As previously discussed, the wireless response signal 44 includes pill identifying information, such as a unique identification code, pharmaceutical content data, manufacturer data and expiration data. The RF tag reader 70 is configured to receive the wireless response signal 44 and the aforementioned data. Additionally, the RF tag reader 70 is configured to transmit the data to the computer 74, whereby the computer 74 displays the data on a monitor 76. Thus, the tube 64 may be used during the ordinary course of pumping or lavaging the stomach 68, with the added benefit of identifying the types and amounts of pills ingested by the individual 62. This aspect of the present invention gives the healthcare provider more detailed information that would allow the healthcare provider to treat the individual 62 more effectively.

Although the present invention has been described with reference to ingestible dosage forms, it is to be understood that the RF tag may be associated with other pills or dosing pharmaceuticals including, but not limited to, suppositories and time release adhesive patches and the like. Furthermore, although the present invention has been described in relation to use of RF tagged pills for ingestion by humans, it is to be understood that various aspects of the present invention may be adapted and applied to animals by manufacturing and utilizing RF tagged pills for such animals.

The invention has been described with reference to the desirable embodiments. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A system for monitoring patient medicine intake compliance and comprising a monitoring device having a unique identifier associated therewith, wherein the monitoring device is designed to be placed within communicative proximity of a plurality of pills each having corresponding RF tags associated therewith, wherein the monitoring device is configured to:

transmit at least one wireless excitation signal at one of a manually initiated and predetermined time, wherein the at least one wireless excitation signal is configured to cause at least one of the plurality of RF tags to transmit a wireless response signal including pill identifying information;

receive the wireless response signal from the at least one RF tag; and transmit the unique identifier of the monitoring device and the pill identifying information of the at least one RF tag, wherein the monitoring device is configured to transmit the unique identifier and the pill identifying information by at least one of wireless, wired, and Internet-based communication links.

2. A device for determining an identity of a pill and quantity thereof ingested by an individual, the device comprising:

one of a nasogastric and orogastric tube having a free gastric end adapted for insertion into a stomach of the individual; and an RF tag reader attached to the free gastric end of one of the nasogastric and orogastric tube, wherein the RF tag reader is configured to:

transmit at least one wireless excitation signal, wherein the at least one wireless excitation signal is configured to cause an RF tag associated with the ingested pill to transmit a wireless response signal including data stored on the RF tag; and receive the wireless response signal from the at least one RF tag.

3. The device of claim 2, further configured to transmit the data to a computer system configured to display the data.

4. The device of claim 2, wherein the data is at least one of a unique identification code, pharmaceutical content data, manufacturer data and expiration data.

* * * * *